United States Patent [19]

Bailey et al.

[11] Patent Number: 5,227,309
[45] Date of Patent: Jul. 13, 1993

[54] C-TERMINAL PEPTIDE SEQUENCING METHOD

[75] Inventors: Jerome Bailey, Duarte; John E. Shively, Arcadia; Narmada R. Shenoy, Torrance, all of Calif.

[73] Assignee: City of Hope, Duarte, Calif.

[21] Appl. No.: 779,303

[22] Filed: Oct. 18, 1991

[51] Int. Cl.$^5$ .............................. G01N 33/68
[52] U.S. Cl. .................... 436/89; 436/175; 436/178; 530/345; 530/408; 530/409; 530/810
[58] Field of Search ............. 436/89, 177, 178, 175; 530/345, 407–410, 810

[56] References Cited

U.S. PATENT DOCUMENTS 5,051,368  9/1991  Boyd et al. ...................... 436/89

Primary Examiner—James C. Housel
Assistant Examiner—David Redding
Attorney, Agent, or Firm—Edward S. Irons

[57] ABSTRACT

A method for the C-terminal sequencing of a peptide in which an alkyl or aryl tin isothiocyanate coupling reagent is used to form a thiohydantoin derivative. Free halogen producing activating agents, such as 2-halo-1-methyl pyridinium salts, may be used as an activating agent for the coupling reagent.

9 Claims, 7 Drawing Sheets

C-TERMINAL PEPTIDE SEQUENCING METHOD

FIELD OF THE INVENTION

This invention relates to the C-terminal sequence analysis of proteins and peptides. More particularly, the invention relates to a novel method for the derivatization of proteins and peptides to provide a C-terminal amino acid thiohydantoin derivative which can be specifically cleaved to yield a thiohydantoin amino acid and a shortened protein or peptide capable of further degradation.

BACKGROUND OF THE INVENTION

Proteins have a central role in all biological processes. The amino acid sequence determines the manner in which protein molecules can fold to form the secondary and tertiary structures important for biological function.

Sequence analysis of peptides and proteins may be accomplished by various known methods. Pursuant to one such method, described in U.S. Pat. No. 4,837,165, C-terminal sequencing is accomplished by reacting a peptide with an isothiocyanate having the chemical formula $R_{(x)}Si(NCS)_y$ where x=0-3, y may be 1-4 and R may be an alkyl c,r aryl substituent. A weak acid anhydride such as acetic anhydride may be mixed with the isothiocyanate. A tertiary amine such as pyridine may be included as a catalyst.

See also U.S. Pat. No. 5,049,507 which describes a C-terminal sequencing reagent comprising a mixed anhydride of isothiocyonic acid and a carboxylic, carbonic: or sulfonic acid.

SUMMARY OF THE INVENTION

This invention provides a novel method for the C-terminal derivatization of proteins and peptides to permit sequence determination by chemical methods. The method of the invention entails C-terminal derivatization of a protein or peptide by reaction with an alkyl or aryl, preferably a trialkyl or triaryl tin isothiocyanate, in the presence of a free halogen producing activating agent such as a 2-halo-1-methyl pyridinium salt.

The thiohydantoin C-terminal amino acid derivative can be specifically cleaved to yield a thiohydantoin amino acid and a shortened peptide. The identity of the released thiohydantoin amino acid is then analyzed, for example, by comparison with the retention times of thiohydantoin amino acid standards on reverse phase HPLC.

DESCRIPTION OF THE FIGURES

FIG. 2 indicates that peak 6 had a MH+ion of 598 indicating that peak 6 was an unreacted starting peptide.

DETAILED DESCRIPTION OF THE PREFERRED PRACTICE OF THE INVENTION

Figure 1:
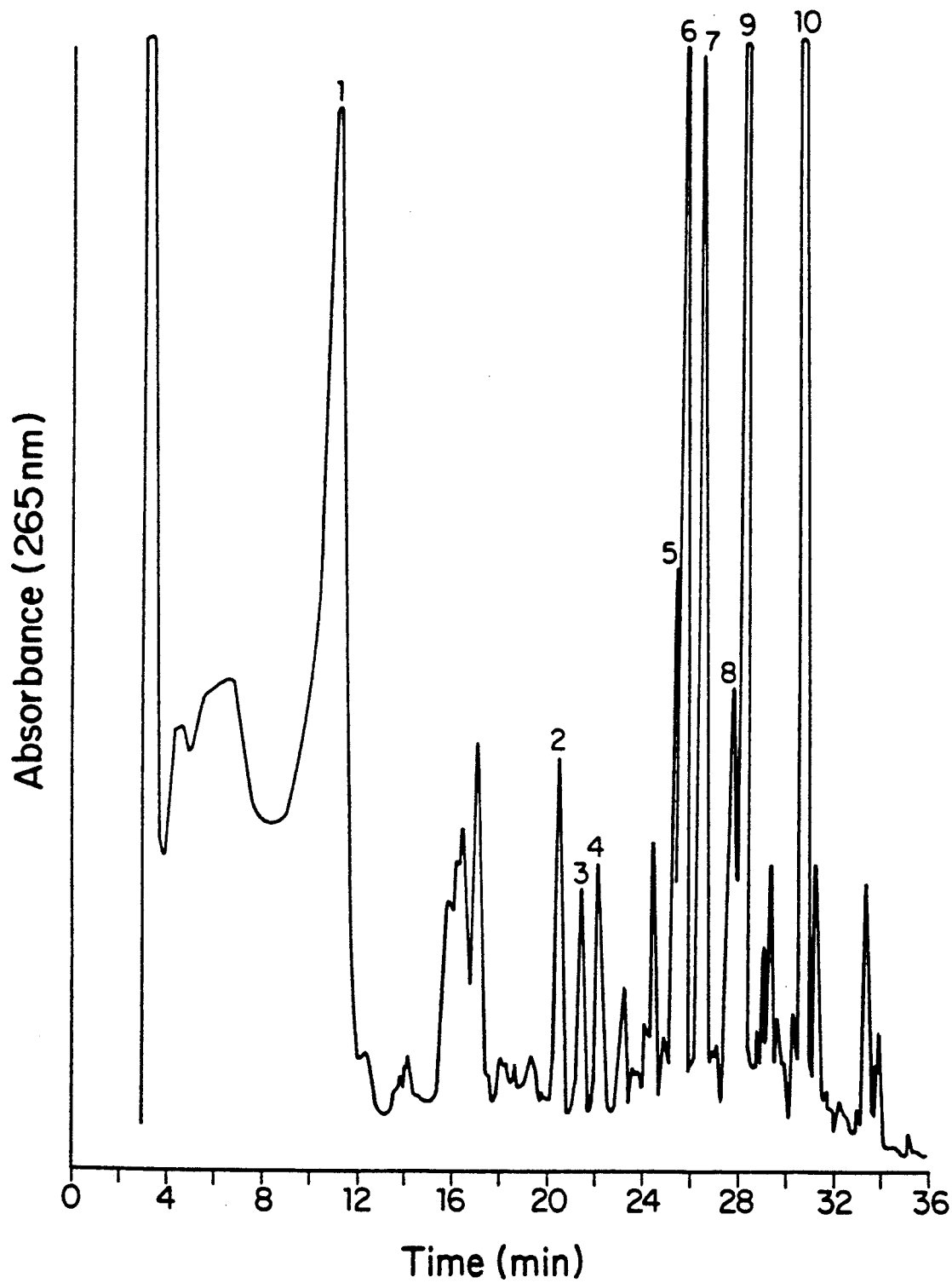
FIG. 1 shows the referenced phase separation of the peptide products obtained in Example 1.

The reagents useful in the method of this invention are alkyl or aryl tin isothiocyanates. In the presence of a free halogen producing activating reagent such as a 2-halo-1-methyl-pyridinium salt, these reagents derivatize peptides or proteins either free in solution or as covalently immobilized or otherwise attached to or supported on to a porous or nonporous support to yield a thiohydantoin amino acid and a shortened peptide or protein capable of continued degradation.

The Alkyl or Aryl Tin

The alkyl or aryl tin reagents have the chemical formula:

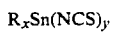

$$R_xSn(NCS)_y$$

in which R is an alkyl or aryl substituent, x is 1, 2 or 3 and y is 3 where x is 1, 2 when x is 2 and 1 when x is 3. Preferably x is 3 and y is 1.

R may be any alkyl or aryl group but preferably is an alkyl group having 1 to 6 carbon atoms, such as a phenyl group or methyl, propyl, isopropyl, n-butyl, isobutyl, n-hexyl and isohexyl group. N butyl groups are preferred. The preferred reagent is tri-n-butyl tin isothiocyanate.

Aluminum or lead atoms be substituted for tin in the reagents useful for the practice of the invention.

The Activating Agent

Activating agents which produce a free halogen are used in conjunction with the alkyl or aryl tin reagent. Reagents of this nature are described by Mukaiyama et al. *Chem. Lett.* 1045-1048 (1975), Mukaiyama Angewandte Chemie 18:707-808 (Eng. Ed.) (1979). The preferred activating reagents are 2-halo-1-methyl pyridinium salts, specifically 2-chloro or 2-fluoro-1-methyl pyridinium iodide. Weak acid anhydrides such as acetic anhydride are not useful as activating agents in the method of this invention.

The Derivatization Reaction

The selected reagent, e.g., tri-n-butyl tin and activating agent, e.g., 2-chloro-1-methyl-pyridinium iodide are dissolved in a suitable solvent such as acetonitrile. Preferably the reagent solution contains from about 1 to about 50% by volume of tri-n-butyl tin isothiocyanate and about 1% to 30% by weight of activating agent.

The protein or peptide sample is preferably covalently attached to a derivatized, activated porous or nonporous polyethylene or PVDF support. Such supports are described in Bailey patent applications PCT/US91/04434, U.S. Ser. Nos. 07/576,943 and PCT/US90/02723. Preferred supports are activated carboxylic acid derivatized porous or non-porous polyethylene films. Such supports are described in application PCT/US91/04434 at page 7 et seq.

The solution of the reagent and activator is applied to the peptide or protein sample either free in solution or covalently attached to the support at a temperature of from about 25° C. to about 90° C., preferably 60° C. for .

about 10 to about 90 minutes, preferably about 20 minutes.

The C-terminal thiohydantoin amino acid produced in this way can be specifically cleaved to yield a thiohydantoin amino acid and shortened peptide.

A proposed mechanism for the derivatization reaction entails release of the —N=C=S ion by reaction of the iodides from 2-chloro-1-methyl pyridinium iodide used for activation of the C-terminal carboxylic acid group. An oxazolinone is then formed which reacts with —N=C=S ion to form a linear isothiocyanate which cyclizes to the desired thiohydantoin amino acid.

The Cleavage Reaction

Specific cleavage to provide a thiohydantoin amino acid and a shortened peptide or protein capable of continued degradation is accomplished in known manner. For example, reaction with dilute aqueous triethylamine as described in Bailey et al Biochem 29, 3145-3156 (1990), or by use of sodium trimethylsilanolate as described in Bailey U.S. patent application Ser. No. PCT/US91/004434.

EXEMPLIFICATION OF THE INVENTION

Example 1

Figure 2:
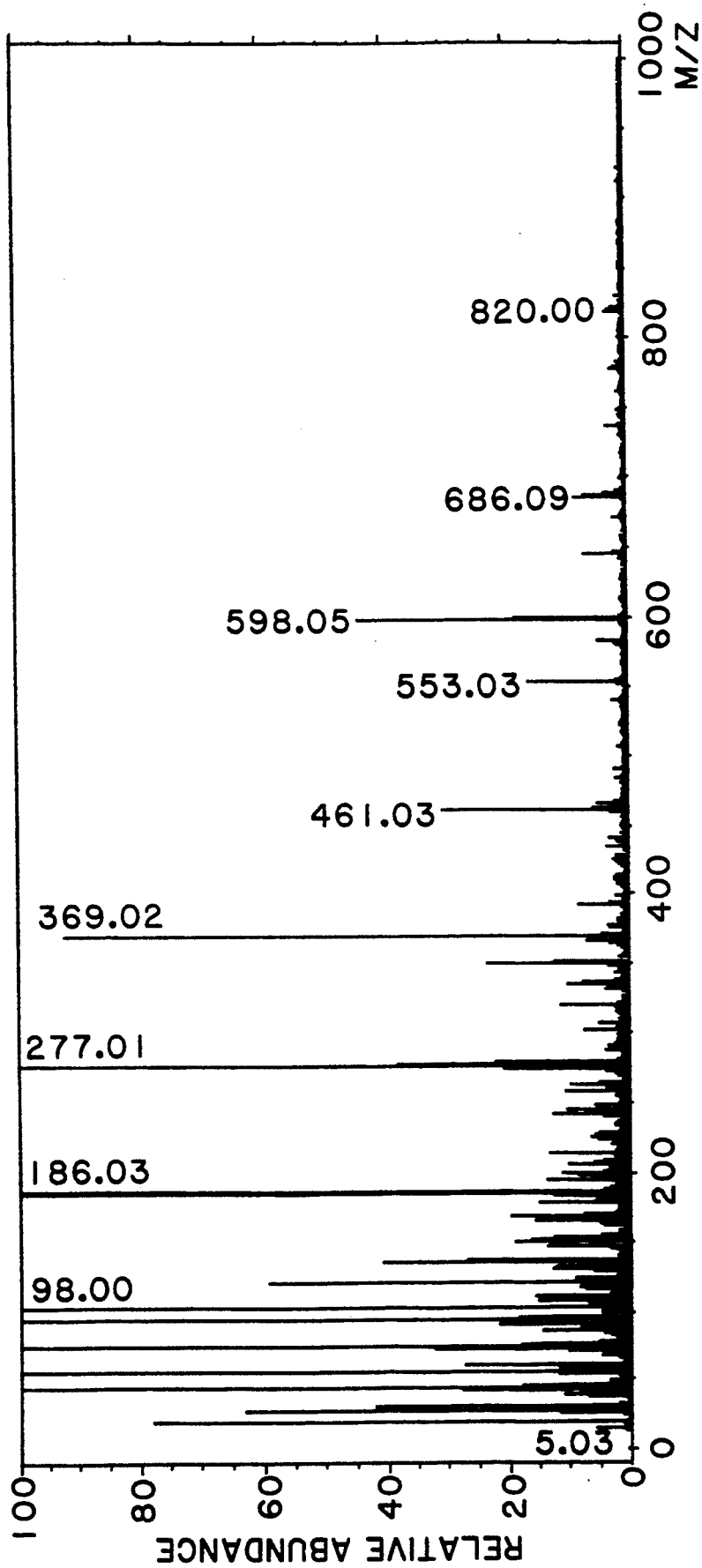
FIG. 2 reflects the FAB/MS of peak 6 of FIG. 1.
Figure 3:
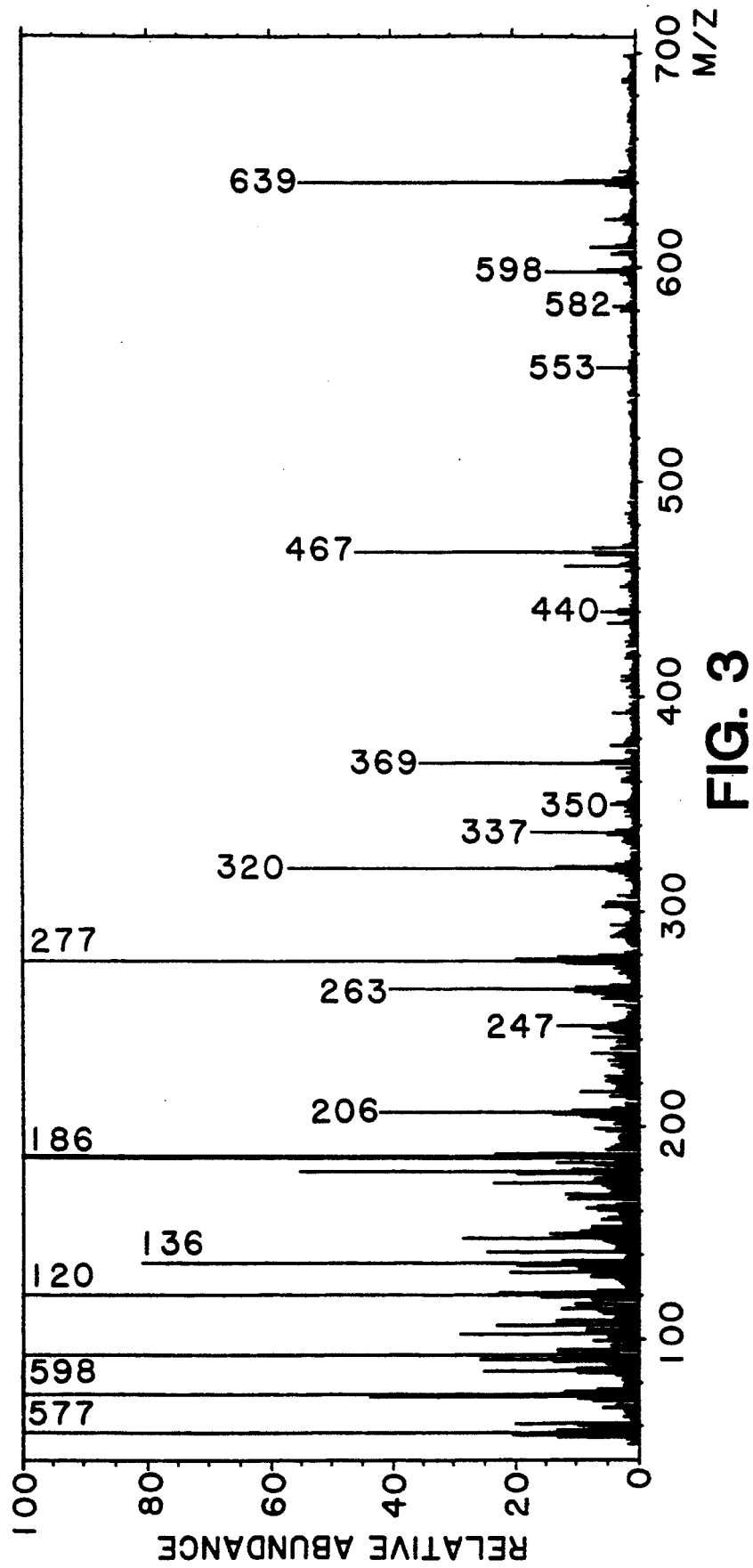
FIGS. 3 and 4 reflect FAB/MS analyses of peaks 9 and 10. These figures indicate that the expected mass (MH+ =639) for the peptidylthiohydantoin, N-acetyl-YGGF-thiohydantoin leucine was obtained.
Figure 4:
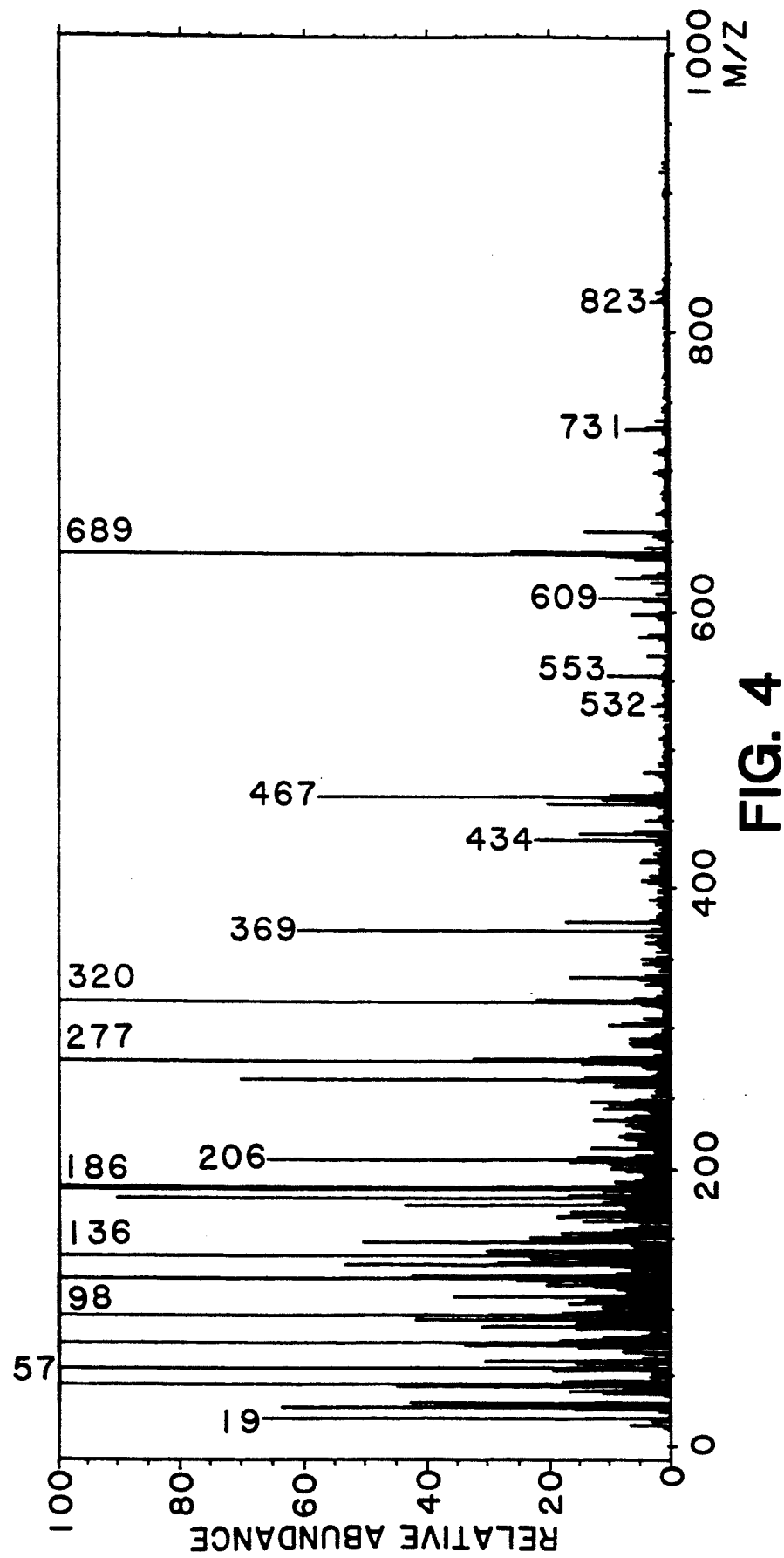

Leucine enkephalin YGGFL (200 nmole) was incubated with acetic anhydride (100μ) in a 1.5 ml eppendorf tube at 50° C. for 10 minutes. The sample was dried under vacuum, dissolved in 10 μl water, and then dried under vacuum. The N-acetylated peptide (YGGFL) was then reacted with 20 μl of 2-chloro-1-methyl pyridinium iodide solution (20 mg in 1 ml acetonitrile), 20 μl tributyltin isothiocyanate, and 200 μl acetonitrile, in a 1.5 ml eppendorf tube at 80° for 20 minutes. The reaction was then taken to dryness with a vacuum centrifugation. The other peaks in FIG. 1 are isothiocyanate degradation products that were incompletely washed off the membrane support. Each numbered peak was then analyzed by FAB/MS. Peak 6 had an MH+ion of 598 indicating that this peak was unreacted starting peptide, N-acetyl YGGFL (FIG. 2). Both peaks 9 and 10 had the expected mass (MG+ =639) for the peptidylthiohydantoin, N-acetyl-YGGF-thiohydantoin leucine (FIGS. 3 and 4, respectively). The presence of two separable peptidylthiohydantoins diastereomers is to be expected if an oxazolinone is formed as an intermediate during the derivatization reaction (Bailey et al, supra).

Example 2

Figure 5:
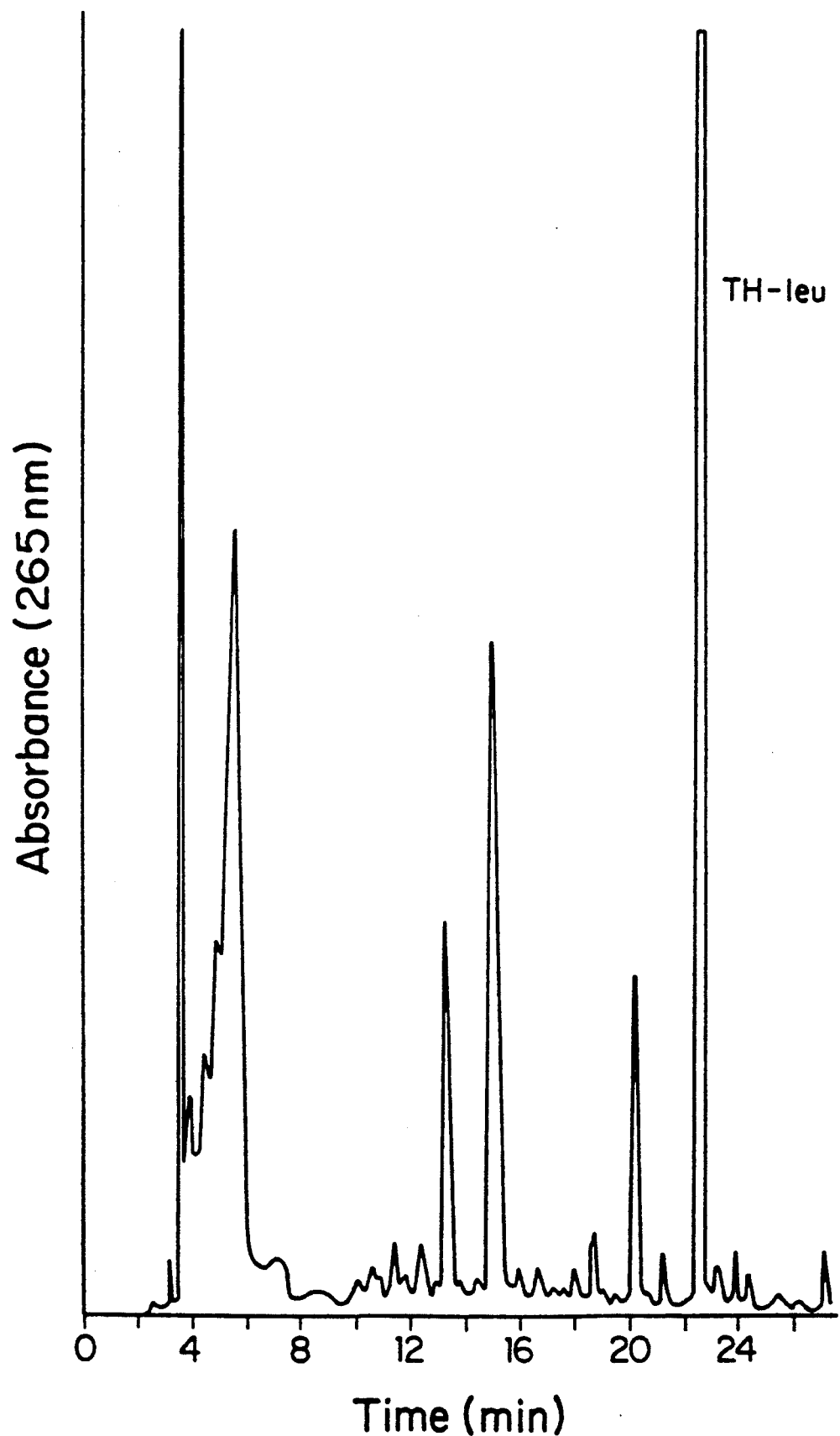
FIG. 5 shows the application of the derivatization chemistry of this invention to YGGFL covalently coupled to carboxylic acid modified polythelene. As FIG. 5 shows a single amino acid, corresponding to the expected thiohydantoin derivative of leucine was obtained.
Figure 6:
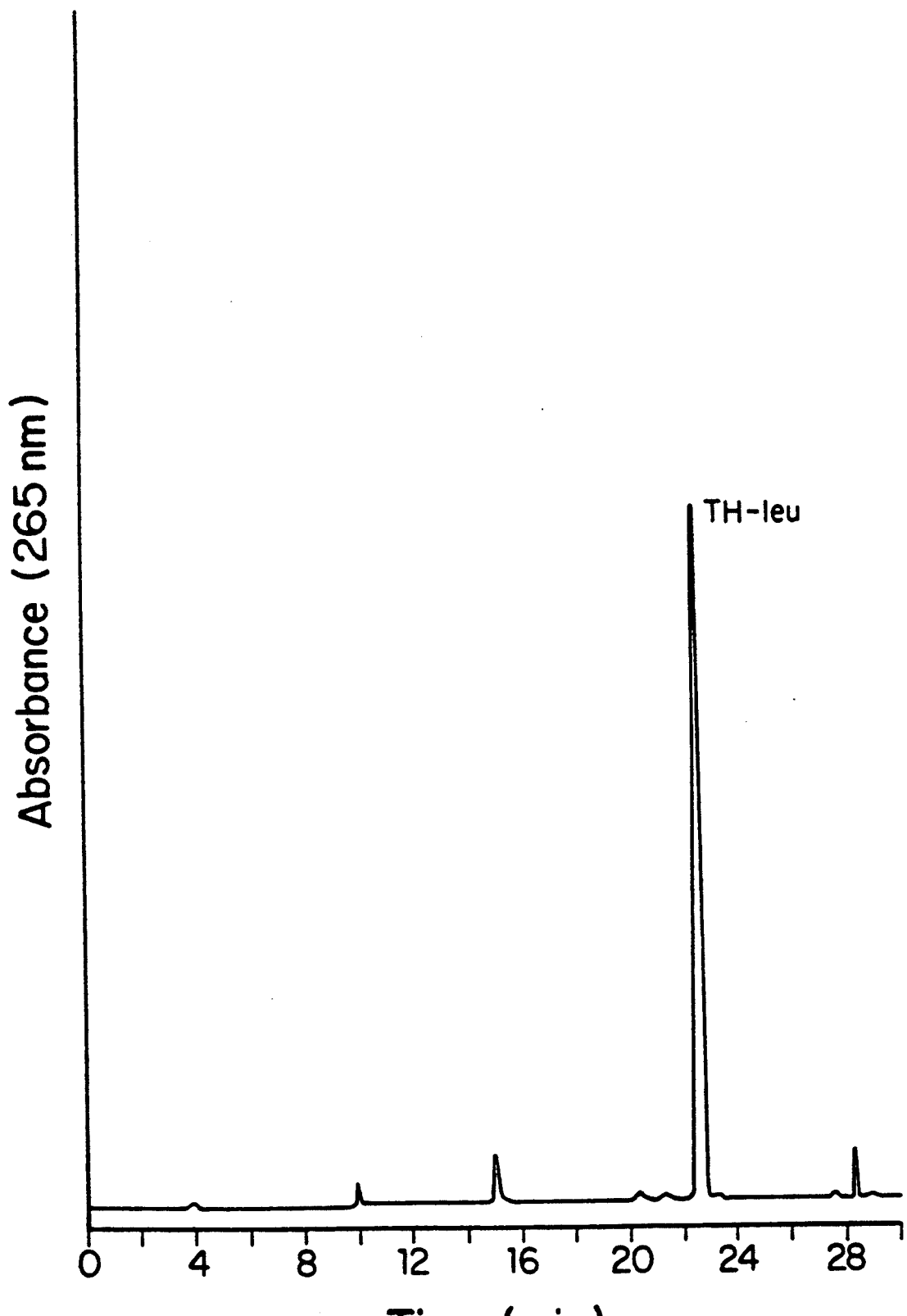
FIG. 6 is a comparison of the retention time of the single amino acid derivative of leucine as compared with the standard HPLC retention time for leucine.
Figure 7:
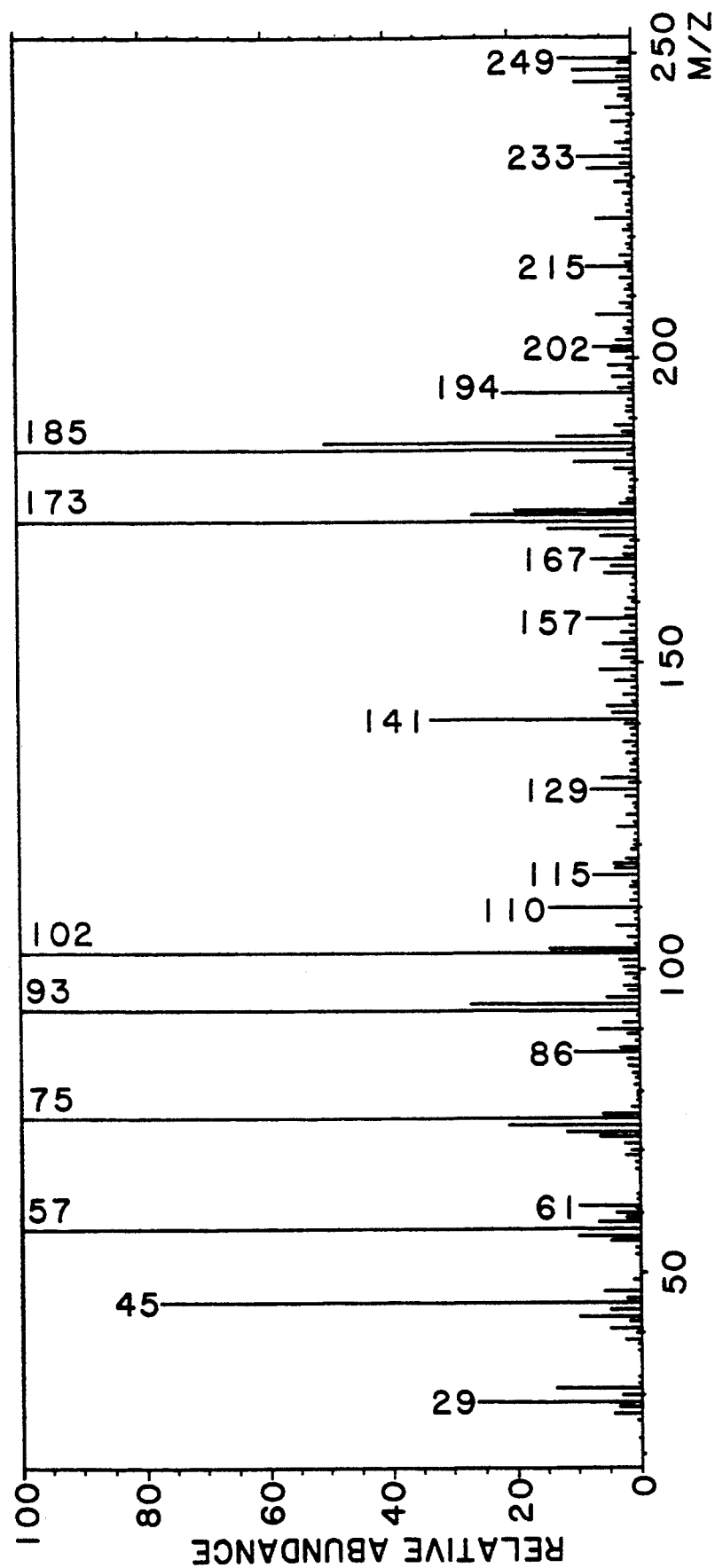
FIG. 7 reflects the expected FAB mass spectrometry analysis of the same derivative.

FIG. 5 shows the application of this novel derivatization chemistry to YGGFL covalently coupled to carboxylic acid modified polyethylene as described in U.S. patent application Ser. No. PCT/US91/04434. A strip of PE-COOH (12.5×1 mm) containing approximately 20 nmol of leucine enkephalin (YGGFL) covalently coupled through the N-terminal amino group was reacted with 2-chloro-1-methyl pyridinium iodide and tributyltin isothiocyanate as described in Example I. At the end of the reaction the strip was washed with 50% aqueous methanol, 0.1% trifluoroacetic acid, 90% acetonitrile in water, and then water. The derivatized C-terminal thiohydantoin amino acid was cleaved with 100 μl of a 5% solution of triethylamine in water for 20 minutes at 50° C. The reaction was dried by vacuum centrifugation and analyzed by reverse phase HPLC. As shown in FIG. 5, a single amino acid, corresponding to the expected thiohydantoin derivative of leucine was obtained. This was confirmed by comparison to the retention times of the amino acid standards (FIG. 6) and by Fab mass spectrometry (FIG. 7). The expected MH+ =ion for thiohydantoin leucine is 173.

We claim:

1. In a method for sequencing a protein or a peptide by carboxyl terminal degradation which comprises coupling the carboxyl terminus of a peptide with a coupling agent to form a thiohydantoin derivative, the improvement which comprises using an alkyl or an aryl tin isothiocyanate as the coupling reagent.

2. A method as defined by claim 1 in which said coupling reagent is an alkyl tin isothiocyanate.

3. A method as defined by claim 1 in which said coupling reagent is tri-n-butyl tin isothiocyanate.

4. A method as defined by any of claim 1, 2 or 3 in which said coupling is accomplished in the presence of an activating agent.

5. A method as defined by any of claims 1, 2 or 3 in which said activating agent is a 2-halo-1-methyl pyridinium salt.

6. In a method for sequencing a protein or a peptide by carboxyl terminal degradation which comprises coupling the carboxyl terminum of a peptide with a coupling agent to form a thiohydantoin derivative, the improvement which comprises using, as the coupling reagent, tri-n-butyl tin isothiocyanate and a free halogen producing activating agent.

7. A method as defined by claim 6 in which said activating agent is 2 chloro-1-methyl pyridinium iodide.

8. An acetonitrile solution of tri-n-butyl tin isothiocyanate and a 2-halo-1-methyl pyridinium salt, said solution containing from about 1% to about 90% by volume acetonitrile, from about 1% to about 30% by volume tri-n-butyl isothiocyanate and from about 1% to about 30% by weight of a 2-halo-1-methyl pyridinium salt.

9. A solution as defined by claim 8 in which said 2-halo-1-methyl pyridinium salt is iodide.

* * * * *